United States Patent
Sevenster et al.

(10) Patent No.: US 9,875,538 B2
(45) Date of Patent: Jan. 23, 2018

(54) REPORTING TOOL WITH INTEGRATED LESION STAGER

(71) Applicant: KONINKLIJKE PHILIPS N.V., Eindhoven (NL)

(72) Inventors: Merlijn Sevenster, Chicago, IL (US); Paul Joseph Chang, Chicago, IL (US)

(73) Assignee: Koninklijke Philips N.V., Eindhoven (NL)

(*) Notice: Subject to any disclaimer, the term of this patent is extended or adjusted under 35 U.S.C. 154(b) by 36 days.

(21) Appl. No.: 14/906,349

(22) PCT Filed: Jul. 28, 2014

(86) PCT No.: PCT/IB2014/063472
§ 371 (c)(1),
(2) Date: Jan. 20, 2016

(87) PCT Pub. No.: WO2015/015393
PCT Pub. Date: Feb. 5, 2015

(65) Prior Publication Data
US 2016/0148374 A1    May 26, 2016

Related U.S. Application Data

(60) Provisional application No. 61/859,423, filed on Jul. 29, 2013.

(51) Int. Cl.
*G06K 9/00* (2006.01)
*G06T 7/00* (2017.01)
(Continued)

(52) U.S. Cl.
CPC ............ *G06T 7/0012* (2013.01); *A61B 5/055* (2013.01); *G06F 19/321* (2013.01);
(Continued)

(58) Field of Classification Search
CPC ................ G06K 9/00; A61B 5/00; G06T 7/00
(Continued)

(56) References Cited

U.S. PATENT DOCUMENTS 7,418,119 B2 *  8/2008  Leichter ................. G06K 9/033
                                                        382/128
8,391,574 B2 *  3/2013  Collins ...................... A61B 8/08
                                                        382/128
(Continued)

OTHER PUBLICATIONS

Friedman, C., et al., "A general natural-language text process for clinical radiology", Journal of the American Medical Informatics Association, vol. 1, No. 2, Mar./Apr. 1994.
Kahn, C.E., et al., "Towards best practices in radiology reporting", Radiology, Sep. 2009;252(3): 852-6.
Cancer Reporting Handbook, Texas Cancer Registry, Jul. 2012, "Recording lab tests and tumor markers in site-specific factors".

*Primary Examiner* — Abolfazl Tabatabai

(57) ABSTRACT

A device and method integrates a lesion stager in a reporting tool. The method includes receiving a user input. The user input is image data including at least one variable value. The variable value is indicative of a variable parameter of the image data. The method includes associating each of the at least one variable value with a corresponding variable parameter to generate at least one variable-value pair. The method includes determining a computed output value as a function of select ones of the at least one variable-value pair.

14 Claims, 3 Drawing Sheets

(51) Int. Cl.
*G06F 19/00* (2011.01)
*A61B 5/055* (2006.01)
*G06K 9/46* (2006.01)
*G06K 9/62* (2006.01)
*A61B 5/05* (2006.01)

(52) U.S. Cl.
CPC ........... *G06F 19/3487* (2013.01); *G06K 9/46* (2013.01); *G06K 9/6202* (2013.01); *G06T 2207/10088* (2013.01); *G06T 2207/30096* (2013.01)

(58) Field of Classification Search
USPC ....... 382/128, 129, 130, 131, 132, 133, 134; 600/407, 410, 411, 425, 427
See application file for complete search history.

(56) References Cited

U.S. PATENT DOCUMENTS

| | | | |
|---|---|---|---|
| 8,761,470 B2* | 6/2014 | Buelow | G06T 7/0012 345/156 |
| RE45,729 E * | 10/2015 | Oh | G06F 17/30079 |
| 9,364,194 B2* | 6/2016 | Hazard | A61B 5/415 |
| 2012/0130223 A1 | 5/2012 | Reicher | |
| 2012/0330876 A1 | 12/2012 | Bryce | |
| 2014/0003697 A1 | 1/2014 | Qian et al. | |

* cited by examiner

REPORTING TOOL WITH INTEGRATED LESION STAGER

CROSS-REFERENCE TO PRIOR APPLICATIONS

This application is the U.S. National Phase application under 35 U.S.C. §371 of International Application No. PCT/IB2014/063472, filed on Jul. 28, 2014, which claims the benefit of U.S. Provisional Application No. 61/859,423, filed on Jul. 29, 2013. These applications are hereby incorporated by reference herein.

A medical image may be generated to determine whether a patient has a medical issue. For example, a magnetic resonance imaging (MRI) may be used to determine if a patient has a mass. In another example, an X-ray may be used to determine if a patient has a lesion, a fracture, etc. When a physician or technician views the medical image, it is possible that varying interpretations may be made from a common image. That is, a report may be made by the physician or technician but the report may include different characteristics of the medical issue. Ideally, if two radiologists interpret the same imaging study, a substantially identical report should be made. However, due to a variety of reasons, this is not always the case. Consumers of reports may get confused if radiologists use different terminology for the same finding, which may lead to suboptimal care or inefficiency such as if an inaccurate exam is ordered.

One of the root causes for inter-radiologist variability is the fact that there are too many reporting guidelines and staging schemes to memorize. A reporting guideline may be a hierarchically related set of instructions that indicate to the user the information that is recommended to be included given the data already obtained. For example, if a user indicates that an imaging study includes a mass, the dimensions of the mass should be included. The physician/technician who creates the report may come to a common conclusion but provide different interpretations such as identifying a mass but describing the mass with different dimensions. The physician/technician may also be unfamiliar with the reporting guidelines/staging schemes that indicate the information that should be included, resulting in such information to be omitted.

With regard to imaging studies, additional schemes or features may be recommended to be used or included. A classification scheme may be utilized in which the classification scheme provides a set of rules that classify a finding in terms of a given, finite number of classes. For example, a grading system for tumors is a typical classification scheme. In another example, a nomogram may be utilized in which the nomogram is a function that returns a value based on input values of various parameters. For example, the nomogram may generate a value for a body/mass index (BMI) in which a person's height and weight are the input values.

Accordingly, it is desirable to reduce inter-radiologist variability when reviewing an imaging study and also integrate the various schemes and nomograms. Thus, there is a need for a reporting tool that reduces inter-radiologist variability and incorporates the various schemes and features.

The present disclosure relates to a device and method for a reporting tool with an integrated lesion stager. The method comprises receiving a user input, the user input being image data or data pertaining to the image's patient extracted from an accessible information management system including at least one variable value, the variable value being indicative of a variable parameter of the data; associating each of the at least one variable value with a corresponding variable parameter to generate at least one variable-value pair; and determining a computed output value as a function of select ones of the at least one variable-value pair.

Figure 1:
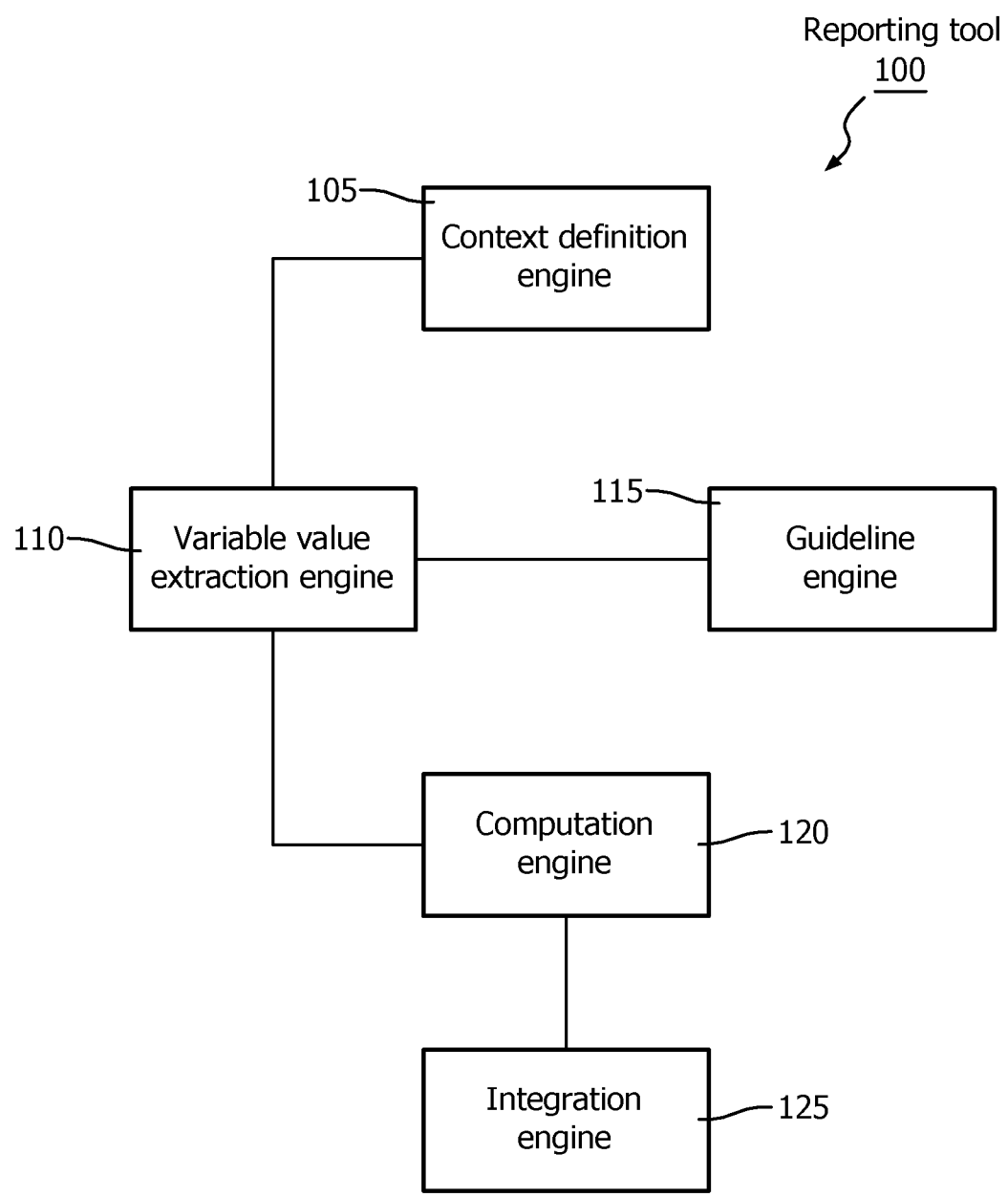
FIG. 1 shows a system for a reporting tool of an imaging study according to the exemplary embodiments.

The exemplary embodiments may be further understood with reference to the following description of the exemplary embodiments and the related appended drawings, wherein like elements are provided with the same reference numerals. The exemplary embodiments are related to a system and method of providing a reporting tool that receives a user input and variable values thereof to generate a computed output value. For example, the user input may relate to a lesion and the variable values may relate to dimensions and a margin of the lesion such that the computed output value is a Breast Imaging-Reporting and Data System (BI-RADS) score. The reporting tool, the user input, the variable values, the computed output value, and a related method will be explained in further detail below.

Initially, it is noted that for concreteness, several assumptions may be made regarding the manner in which the computed output value is generated. For example, a domain of finite number of variable values may be made. That is, the variable values associated with the user input may be defined with a predetermined number such that the variable values relate to selected parameters of the user input. Specifically, with regard to a lesion, each variable is a parameter from a given set such as "lesion size" or "calcification" and the values thereof are real values, such as 2.0, or objects from a normalized list such as microcalification, calcification, large calcification, none, etc. In another example, each variable value is assigned a default value which is unknown and is provided by the user. Accordingly, the manner of generating the computed output value integrates one classification scheme or nomogram and generation of the computed output value is treated as a mathematical function that accepts the user input having at least one or potentially all of the predetermined variable values. However, it should be noted that the exemplary embodiments may also relate to a process in which the above noted assumptions are not made. For example, the variable values may not have a predetermined number and other variable values that would otherwise not be utilized may be provided by the user or determined.

FIG. 1 shows a system for a reporting tool 100 of an imaging study according to the exemplary embodiments. The reporting tool 100 is configured to receive a user input such that a predetermined set of variable values are defined as a function of the user input. The reporting tool 100 subsequently receives select variable values. The reporting tool 100 determines whether the select variable values are satisfactory to generate a computed output value. If at least one further variable value is required, a request is made such that the further variable value is received. When sufficient variable values are received, the reporting tool 100 generates the computed output value. The reporting tool 100 includes a context definition engine 105, a variable value extraction engine 110, a guideline engine 115, a computation engine 120, and an integration engine 125.

The context definition engine 105 receives a user input. The user input may be in a variety of manners such as an image. In a specific exemplary embodiment, the image is a MRI, X-ray, etc. The image is an initial user input provided by the user. Within this initial user input, there may further include a variety of associated information. That is, additional user input is provided with the initial user input. In a first example, there may be image annotations. Accordingly, the annotations in the image may be considered by the context definition engine 105 such as a dimensional or angular measurement, an arrow, a box, a graphical item attached to the image, etc. In a second example, free text may be included in the user input. Accordingly, text that may be dictated or typed by the user is considered by the context definition engine 105. In a third example, structured content may be included in the user input. Accordingly, an object of structured context is considered by the context definition engine 105 such as an XML object. The context definition engine 105 is alerted that an XML object should be taken as context via a standard user interface means (e.g., a button). Therefore, the context definition engine 105 extracts the information that is included in the user input.

It should be noted that prior to the context definition engine 105 receiving the user input, the user may manually enter the further information in the user input using the above noted examples. Accordingly, the user may initially view the user input such as an image (e.g., MRI) and make measurements or perform other forms of information gathering. The user may then include the information in the user input prior to the context definition engine 105 receiving the user input.

The context definition engine 105 also restricts a scope of the available information associated with a use of the reporting tool 100. In a first example, the reporting tool 100 relates to a particular functionality. Accordingly, the context definition engine 105 limits the information from the user input to the parameters defined therein. In a specific exemplary embodiment, if the user input includes image annotations, select ones of the annotations are considered if pertaining to the functionality while others are omitted. In a second example, the reporting tool 100 determines the functionality associated with the user input upon receiving it. Accordingly, the context definition engine 105 receives the user input and subsequently defines the parameters of the information associated therewith in an ad hoc manner. Therefore, the context definition engine 105 restricts the information to pertinent data that is used subsequently as a function of the reporting tool 100 or the user input.

The variable value extraction engine 110 generates a mapping from variable parameters to its respective value. Initially, it is noted that, depending on the context, select variable parameters may be considered, of which further select ones thereof have a higher relevance or priority than others. The variable value extraction engine 110 extracts the values received by the context definition engine 105 and associates these values with the appropriate variable parameter. Once all values from the context definition engine are associated with its variable parameter, the variable value extraction engine 110 uses a default value (e.g., "?") if no value is obtained for certain variable parameters. It is noted that an actual real number is not used as a zero (0) value may be indicative of an actual value to associate with a particular variable parameter.

As discussed above, the context definition engine 105 receives a user input having a variety of information associated therewith such as an image annotation, a free text, and a structured content. With particular regard to these examples, the variable value extraction engine 110 associates the values included in this user input information with its appropriate variable parameter, thereby extracting a variable-value vector from the content. In the first example of image annotations, imaging features are extracted such as a length or surface of a measurement, an angle of two lines, a surface of a box, etc. The variable value extraction engine 110 directly extracts these values from the user input. In another exemplary embodiment, the variable value extraction engine 110 automatically extracts additional features from the user input when not specifically denoted in the information included therein. For example, a contour analysis is extracted. In a further exemplary embodiment, the variable value extraction engine 110 receives a particular annotation that requires further input. For example, if the user draws a box via a user interface in the image received by the context definition engine 105, the variable value extraction engine 110 requests additional information such as the particular variable parameter the box defines (e.g., tumor, cyst, hemorrhage, etc.). In the second example of free text, the variable value extraction engine 110 includes a natural language processing engine that automatically extracts values from the selected text. In a specific example, the selected text is normalized against a background vocabulary such as SNOMED CT or RadLex. The natural language processing engine further uses a negation detection application or other application that interconnects extracted findings to increase a granularity of the information extraction. In the third example of structured content, since the content is structured, a query in the content's native language is used for the information extraction.

The guideline engine 115 is used to determine whether further information is required. That is, the guideline engine 115 fills gaps in the information extraction that has been performed. For example, when three (3) parameter values are required to determine a computed output value but only two (2) parameter values are received or extracted, the guideline engine 115 requests that the third parameter value be entered. Accordingly, the guidelines engine 115 is configured with predetermined settings or rules to verify if at least one value and associated variable parameter is satisfactory to generate the computed output value.

The guideline engine 115 receives the extracted values and the associated variable parameter from the variable value extraction engine 110. In a specific exemplary embodiment, the guideline engine 115 relates to a Boolean value indicating whether the extracted values and the associated variable parameter is satisfactory to generate the computed output value. If the guideline engine 115 returns a "yes" or "satisfactory" value, the variable value extraction engine 110 has all the necessary information. Conversely, if the guideline engine 115 returns a "no" or "unsatisfactory" value, the variable value extraction engine 110 still requires at least one further value to associate with the variable parameter. The guideline engine 115 further includes which of the at least one further value is required. Thus, upon receiving this information, the variable vector extraction engine 110 requests the user for the at least one further value.

The guideline engine 115 is further configured with a Help-functionality. Specifically, the Help-functionality relates to the predetermined settings or rules that indicate whether values and variable parameters result in a "satisfactory" response. The user may utilize a user interface to access the Help-functionality. In a first exemplary embodiment, the guideline engine 115 determines the relevant predetermined settings/rules that the user may be requesting as a function of the user input and/or the extracted values. In a second exemplary embodiment, the guideline engine 115 provides a menu for the user to select the relevant predetermined settings/rules. Subsequently, the user may view the predetermined settings/rules to aid in determining whether the extracted values for the associated variable parameter will result in a "satisfactory" response.

The computation engine 120 generates the computed output value as a function of the variable values and its associated variable parameter. The computation engine 120 receives the variable values and the associated variable parameter to generate the computed output value. The computed output value may be a class or value based on algebraic computations or statistical estimations preprogrammed into the computation engine 120. The computation engine 120 may generate the computed output value in a variety of manners. For example, the computed output value may be an XML object that indicates the formula being used, the value, the units thereof, etc. In another example, the computation engine 120 generates the computed output value with free text or as an annotation.

The integration engine 125 integrates the computed output value in a report that is created for the user input. The integration engine 125 receives the computed output value such as an XML object and integrate its semantics with a workflow. This may be done in a variety of manners. In a first example, the computed output value is returned to the user such that the user is able to view the outcome. In a second example, the computed output value is automatically inserted into the report such as the XML object being converted to natural language and inserted into a suitable area in the report. In a third example, the computed output value is attached as metadata.

It should be noted that the reporting tool 100 may be configured to determine further output data. For example, the computation engine 120 may also generate follow-up or treatment data that is derived from the computed output value, the extracted values with the associated variable parameter, additional received values, etc. The computation engine 120 may also generate this further output data in the variety of manners discussed above.

Figure 2:
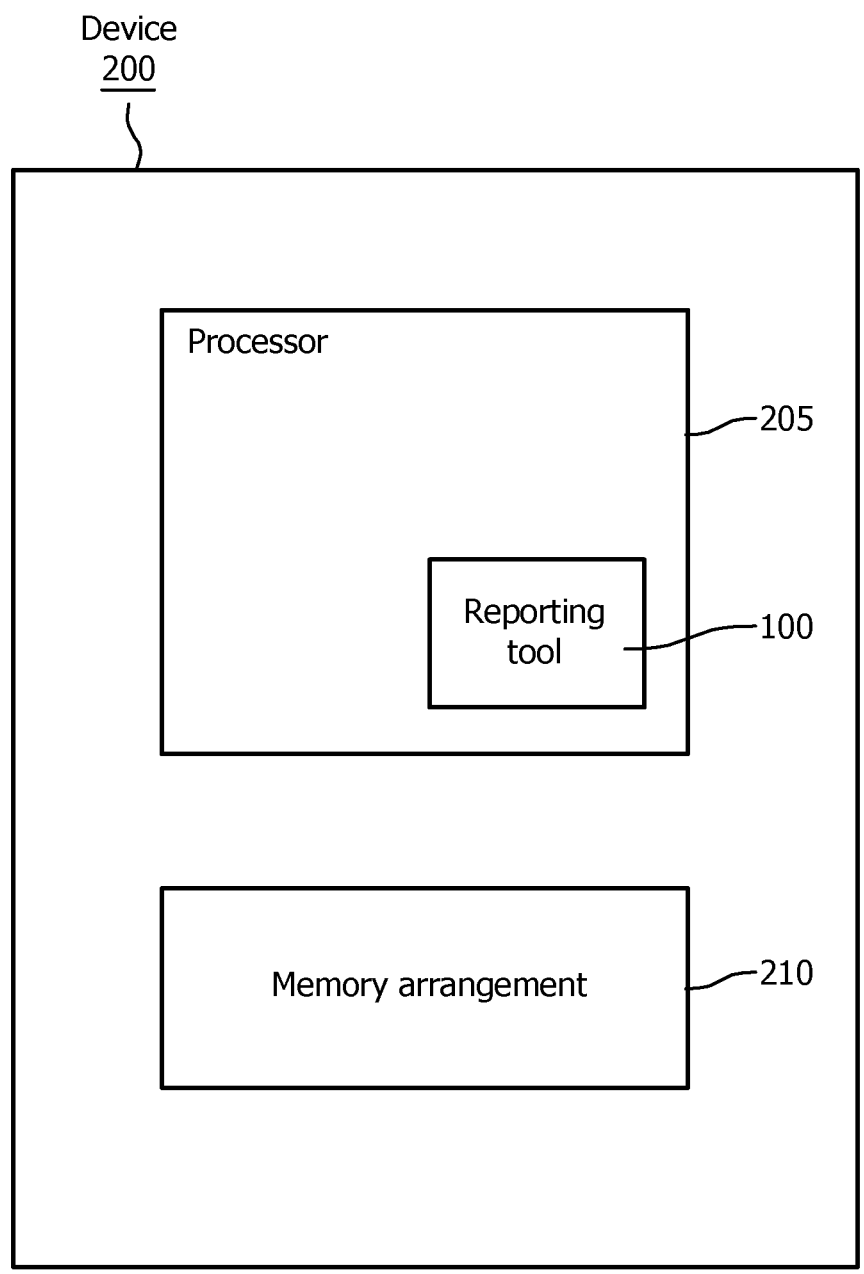
FIG. 2 shows a device incorporating the reporting tool of FIG. 1 according to the exemplary embodiments.

It should also be noted that the reporting tool 100 may be a processor configured to perform the above described manner of generating the computed output value. FIG. 2 shows a device 200 incorporating the reporting tool 100 of FIG. 1 according to the exemplary embodiments. The device 200 includes a processor 205 that incorporates the reporting tool 100 including the context definition engine 105, the variable value extraction engine 110, the guideline engine 115, the computation engine 120, and the integration engine 125. The device 200 also includes a memory arrangement storing the data related to the reporting tool 100. For example, the user input that is received by the context definition engine 105 is stored thereon, the extracted values of the variable value extraction engine 110 is stored thereon, the settings/rules of the guideline engine 115 is stored thereon, etc.

According to the exemplary embodiments, the reporting tool 100 generates at least one computed output value as a function of the values extracted from a user input and/or user input values entered by the user. The reporting tool 100 may relate to a variety of different types of context. In a specific example, the reporting tool 100 is used in relation to a breast MRI. As a preliminary step, a radiologist views the breast MRI. The radiologist may determine that there is a lesion and measurements of the lesion may be made by the user. The user includes the measurements in the breast MRI as an annotation, using free text, as structured content, etc. Subsequently, the reporting tool 100 is utilized such that the context definition engine 105 receives the breast MRI with the measurement data of the lesion. The context definition engine 105 determines the received user input is the image (e.g., breast MRI) and further determines the relevant information to be considered. The variable value extraction engine 110 extracts the dimensions of the lesion (e.g., 2 cm×3 cm) from the included information (e.g., annotation, free text, structured content, etc.). The variable value extraction engine 110 also associates the measurement data with the variable parameter of dimensions. Accordingly, a variable-value pair <dimension value="2 cm×3 cm"/> may be added to the information vector of the user input. The guideline engine 115 receives the variable-value pair and determines that the extracted information does not include a value for margin of the lesion. Accordingly, the guideline engine 115 returns an "unsatisfactory" result to the variable value extraction engine 110 indicating that the margin value is missing. The variable value extraction engine 110 requests for this missing information from the user. The user enters a further user input value of this information using any of the aforementioned manners and indicates that the margin value is specified such as "spiculated." The variable value extraction engine 110 associates this value with the appropriate variable parameter such that a variable-value pair <margin="spiculated"/> is also added to the information vector of the user input. This process continues until the guideline engine 115 returns a result that the information vector is "satisfactory" (i.e., sufficiently complete for computations). Once this result is received by the variable value extraction engine 110, the computation engine 120 receives the information vector including the variable values and associated variable parameters. Subsequently, the computation engine 120 determines the computed output value such as BI-RADS score of the lesion. For example, given the dimensions and margin of the lesion, the computation engine 120 may determine a BI-RADS score of two (2). The computation engine 120 may further determine a further output value such as a recommended treatment. For example, the computation engine 120 may determine a yearly follow-up is recommended. In another example, the computation engine 120 includes other output values such as a background information section (e.g., a URL). Finally, the integration engine 125 receives the computed output value and the further output data from the computation engine 120 such that a structured content such as an XML object is generated and included in a report for the breast MRI. The integration engine 125 further incorporates the variable values and the associated variable parameters in the report as an XML object.

Figure 3:
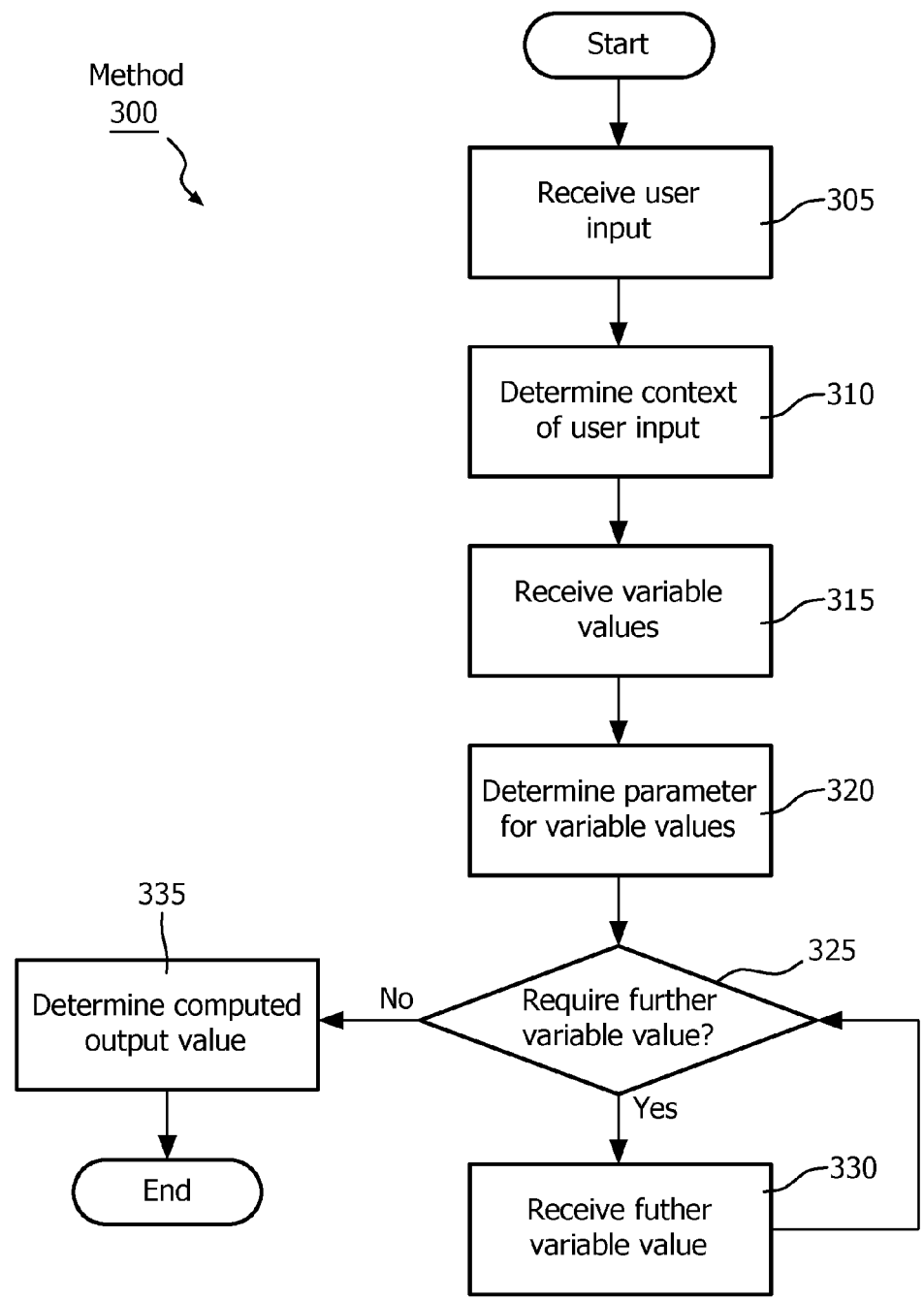
FIG. 3 shows a method of generating data from a reporting tool of an imaging study according to the exemplary embodiments.

FIG. 3 shows a method 300 of generating data from a reporting tool of an imaging study according to the exemplary embodiments. Specifically, the method 300 relates to receiving a user input that includes information and requesting/receiving further necessary information such that a computed output value is determined as a function thereof. Accordingly, prior to the method 300, the user may include the information in the user input. The method 200 will be discussed with reference to the reporting tool 100 of FIG. 1.

In step 305, the context definition engine 105 receives the user input. As discussed above, the user input may be a variety of types such as an image. Thus, the reporting tool 100 may relate to an imaging study. In step 310, the context definition engine 105 determines the context of the user input. As discussed above, the context definition engine 105 may automatically determine the context in which the user input relates, thereby restricting the relevant information that is to be considered. In another example, the context definition engine 105 may be predetermined for a particular context and have predetermined settings to restrict the relevant information. In yet another example, the context definition engine 105 may be manually set by the user for the particular context and may further be manually set to restrict the relevant information.

In step 315, the variable value extraction engine 110 receives and/or extracts the variable values associated with the user input. As discussed above, the user input may include information such as annotations, free text, structured content, etc. The variable value extraction engine 110 extracts the variable values therein. The variable value extraction engine 110 also receives variable values that may be entered by the user. Thus, in step 320, the variable value extraction engine 110 determines the variable parameter in which the variable values are to be associated. For example, if a variable value is "2 cm×3 cm," the variable value extraction engine 115 pairs this variable value with the variable parameter of "dimensions."

In step 325, a determination is made by the guideline engine 115 whether a further variable value or variable parameter is required. Specifically, the guideline engine 115 is programmed with predetermined settings and/or rules to make this determination. In the above example of dimensions, the guideline engine 115 determines that a variable value for margin is also required. Thus, the method 300 continues to step 330 where the variable value extraction engine 110 requests the user to provide this variable value. The user enters the margin variable value as "spiculated." This process continues until the guideline engine 115 indicates that no further variable value is required. The method 300 then continues to step 335 where the computation engine 120 receives the variable-value pairs (i.e., variable values and associated variable parameter) in order to determine a computed output value as a function thereof.

It should be noted that the steps described above for the method 300 is only exemplary. The method 300 may include additional steps. For example, after step 335, the method 300 may include a step of integrating the computed output value in a report. Specifically, the integration engine 125 may integrate the computed output value as an XML object in the report at a predetermined or selected area. In another example, if step 325 determines further variable values are required, the method 200 may include a step of returning a Boolean result and including the further variable value that is required. In yet another example, after step 335, the method 300 may include another step of determining further output values such as treatment recommendations and background information. Thus, utilizing the above noted step of including the computed output value in the report, this step may further include this value/information in the report. In a further example, the method 300 may include a step of receiving a user entry indicating the manner in which the report is to be generated. For example, the user may indicate that the computed output value is to be included in a specific format (e.g., annotation, free text, etc.). In yet another further example, the method 300 may include a step of assigning a default unknown value to variable parameters that are not associated with a variable value. Thus, the guideline engine 115 may be aware of select variable parameters that are necessary for the computed output value to be generated.

The exemplary embodiments provide a system and method to generate a computed output value from variable values and associated variable parameters that are extracted and/or received from a user and/or user input. The variable values are extracted from information included in the user input. The extracted variable values are also selected for extraction as a function of the context in which the user input relates. The computed output value may ultimately be integrated into a report that is created for the user input.

Those skilled in the art will understand that the above-described exemplary embodiments may be implemented in any suitable software or hardware configuration or combination thereof. An exemplary hardware platform for implementing the exemplary embodiments may include, for example, an Intel x86 based platform with compatible operating system, a Mac platform and MAC OS, etc. In a further example, the exemplary embodiments of the reporting tool may be embodied as a program containing lines of code stored on a non-transitory computer readable storage medium that, when compiled, may be executed on a processor.

It will be apparent to those skilled in the art that various modifications may be made in the present invention, without departing from the spirit or the scope of the invention. Thus, it is intended that the present invention cover modifications and variations of this invention provided they come within the scope of the appended claims and their equivalent.

What is claimed is:

1. A method, comprising:
   receiving, by a processor, a user input, the user input being medical image data including at least one variable value, the variable value being a measurement of a feature of the medical image data indicative of a variable parameter of the medical image data,
   wherein the variable parameter is a required parameter for determining a computed output value;
   associating, by the processor, each of the at least one variable value with a corresponding variable parameter to generate at least one variable-value pair;
   determining, by the processor, whether at least one further variable-value pair is required to determine the computed output value;
   determining, by the processor, select ones of the at least one further required variable-value pair;
   requesting, by a user interface, for the select ones of the at least one further required variable-value pair;
   receiving, by the user interface, the select ones of the at least one further required variable-value pair; and
   determining, by the processor, the computed output value as a function of select ones of the at least one variable-value pair and select ones of the at least one further required variable-value pair.

2. The method of claim 1, further comprising:
   determining, by the processor, a context of the user input; and
   extracting, by the processor, select ones of the at least one variable value from the user input as a function of the context.

3. The method of claim 1, wherein the determination for at least one further variable-value pair is a function of at least one of predetermined settings and predetermined rules.

4. The method of claim 1, further comprising:
   integrating, by the processor, the computed output value in a report for the user input.

5. The method of claim 1, wherein the at least one variable value is included in the user input as at least one of an annotation, a free text, and a structured content.

6. The method of claim 1, further comprising:
   determining, by the processor, at least one further computed output value as a function of the computed output value.

7. The method of claim 1, wherein the medical image data is a magnetic resonance imaging (MRI), the at least one variable value is a width and length of a lesion, the variable parameter is dimensions of the lesion, and the computed output value is a Breast Imaging-Reporting and Data System (BI-RADS) score.

8. A reporting tool, comprising:
a processor configured to receive a user input, the user input being medical image data including at least one variable value, the variable value being a measurement of a feature of the medical image data indicative of a variable parameter of the medical image data, wherein the variable parameter is a required parameter for determining a computed output value; and
a memory arrangement configured to store the user input, the at least one variable value, and the variable parameter,
wherein the processor is configured to associate each of the at least one variable value with a corresponding variable parameter to generate at least one variable-value pair,
wherein the processor is configured to determine whether at least one further variable-value pair is required to determine the computed output value, determine select ones of the at least one further required variable-value pair, request for the select ones of the at least one further required variable-value pair, and receive the select ones of the at least one further required variable-value pair, and
wherein the processor is configured to determine the computed output value as a function of select ones of the at least one variable-value pair and select ones of the at least one further required variable-value pair.

9. The reporting tool of claim 8, wherein the processor is configured to determine a context of the user input and extract select ones of the at least one variable value from the user input as a function of the context.

10. The reporting tool of claim 8, wherein the determination for at least one further variable-value pair is a function of at least one of predetermined settings and predetermined rules.

11. The reporting tool of claim 8, wherein the processor is configured to integrate the computed output value in a report for the user input.

12. The reporting tool of claim 8, wherein the at least one variable value is included in the user input as at least one of an annotation, a free text, and a structured content.

13. The reporting tool of claim 8, wherein the processor is configured to determine at least one further computed output value as a function of the computed output value.

14. A non-transitory computer readable storage medium storing a set of instructions that are executable by a processor, the instructions causing the processor to:
receive a user input, the user input being medical image data including at least one variable value, the variable value being a measurement of a feature of the medical image data indicative of a variable parameter of the medical image data,
wherein the variable parameter is a required parameter for determining a computed output value;
associate each of the at least one variable value with a corresponding variable parameter to generate at least one variable-value pair;
determine whether at least one further variable-value pair is required to determine the computed output value;
determine select ones of the at least one further required variable-value pair;
request for the select ones of the at least one further required variable-value pair;
receive the select ones of the at least one further required variable-value pair; and
determine the computed output value as a function of select ones of the at least one variable-value pair and select ones of the at least one further required variable-value pair.

* * * * *